United States Patent [19]

Shimizu et al.

[11] Patent Number: 5,679,746
[45] Date of Patent: Oct. 21, 1997

[54] SILACYCLOHEXANE COMPOUND, A METHOD OF PREPARING IT AND A LIQUID CRYSTAL COMPOSITION CONTAINING IT

[75] Inventors: Takaaki Shimizu; Tsutomu Ogihara; Kazuyuki Asakura; Takeshi Kinsho; Tatsushi Kaneko; Mutsuo Nakashima, all of Kubiki-mura, Japan

[73] Assignee: Shin-Etsu Chemical Co., Ltd., Tokyo, Japan

[21] Appl. No.: 576,619

[22] Filed: Dec. 21, 1995

[30] Foreign Application Priority Data

Dec. 22, 1994 [JP] Japan .................................. 6-336182
Dec. 22, 1994 [JP] Japan .................................. 6-336183

[51] Int. Cl.$^6$ ........................... C09K 19/34; C07F 7/08
[52] U.S. Cl. ................ 252/299.61; 556/406; 252/299.63
[58] Field of Search ........................ 252/299.61, 299.63; 556/406

[56] References Cited

U.S. PATENT DOCUMENTS

| | | | |
|---|---|---|---|
| 5,454,977 | 10/1995 | Shimizu et al. | 252/299.61 |
| 5,496,501 | 3/1996 | Shimizu et al. | 252/299.61 |
| 5,523,440 | 6/1996 | Nakashima et al. | 556/406 |
| 5,527,490 | 6/1996 | Kinsho et al. | 252/299.61 |
| 5,560,866 | 10/1996 | Ogihara et al. | 252/299.61 |
| 5,567,350 | 10/1996 | Shimizu et al. | 252/299.61 |

FOREIGN PATENT DOCUMENTS

| | | |
|---|---|---|
| 014840 | 9/1980 | European Pat. Off. . |
| 194879 | 9/1986 | European Pat. Off. . |
| 630903 | 12/1994 | European Pat. Off. . |
| 632044 | 1/1995 | European Pat. Off. . |
| 673942 | 9/1995 | European Pat. Off. . |

OTHER PUBLICATIONS

T. Sadao, H. Takatsu, Preparation of (Fluoroalkyl)cyclohexane Derivatives as Liquid Crystals, Jan. 9, 1995, *Chemical Abstracts*, vol. 122, No. 2, p. 833.

Primary Examiner—C. H. Kelly
Attorney, Agent, or Firm—Townsend & Banta

[57] ABSTRACT

A silacyclohexane compound represented by the following general formula (I):

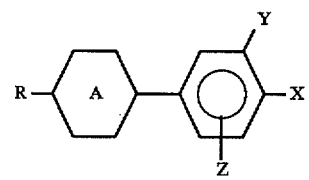

wherein R denotes a mono- or di-fluoroalkyl group with 1–10 carbons:

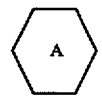

denotes a trans-1-silacyclohexylene or a trans-4-silacyclohexylene group whose silicon at position 1 or position 4 has a substitutional group of H, F, Cl or $CH_3$;

X denotes a CN, F, Cl, $CF_3$, $CF_2Cl$, CHFCl, $OCF_3$, $OCHF_2$, $OCF_2Cl$, OCHFCl, $(O)_sCY_1=CX_1X_2$ ($X_1$ and $Y_1$ denote H, F or Cl, and $X_2$ denotes F or Cl) $(O)_sC_pH_qF_r$ (p denotes 2, 3 or 4, and q and r are integers which satisfy the equation q+r=2p+1, and s denotes 0 or 1), the aforementioned R, or an alkyl or alkoxy group with 1–5 carbons;

Y denotes H or F; and

Z denotes H or F;

and process of manufacturing same.

11 Claims, No Drawings

SILACYCLOHEXANE COMPOUND, A METHOD OF PREPARING IT AND A LIQUID CRYSTAL COMPOSITION CONTAINING IT

RELATED APPLICATION

This application claims the priority of Japanese Patent applications No. 8-386182 filed on Dec. 22, 1994 and No. 6-386183 filed on Dec. 22, 1994, which are incorporated herein by reference.

BACKGROUND OF THE INVENTION

1. Field of the Invention

This invention relates to a new silacyclohexane compound, a method of preparing it, and a liquid crystal composition which contains it, as well as a liquid crystal display element containing said liquid crystal composition.

2. The prior Art

A liquid crystal display element utilizes the optical anisotropy and dielectric anisotropy of liquid crystal substances. Display methods include the TN mode (twisted nematic mode), the STN mode (super twisted nematic mode), the SBF mode (super birefringence mode), the DS mode (dynamic scattering mode), the guest-host mode, the DAP mode ("deformation of aligned phase" mode) and the OMI mode (optical mode interference mode). The most common display device has a twisted nematic structure based on the Schadt-Helfrich mode.

The properties required of the liquid crystal substance used in these liquid crystal displays are somewhat different depending on the display method. However, a wide liquid crystal temperature range and stability with regard to moisture, air, light, heat, electric fields, etc., are properties commonly required by all display methods. Furthermore, it is desirable for the liquid crystal material to have a low viscosity, and also to have a short address time, low threshold voltage and high contrast in the cell.

Currently, there is no single compound which satisfies all these requirements. In practice, liquid crystal mixtures are used which are obtained by mixing several to more than ten liquid crystal compounds and latent liquid crystal compounds. Because of this, it is also important that the components of a liquid crystal composition mix easily.

The liquid crystal compound which can be components of these are classified into several categories based on their functions, as shown below:

1) Compounds which contribute to a reduction in viscosity and a lowering of the melting point of the mixed liquid crystal composition;
2) Compounds which mainly control the electro-optical functions of the mixed liquid crystal composition
3) Compounds which contribute to raising the clearing point of the mixed liquid crystal composition;
4) Compounds which contribute to refraction anisotropy control of the mixed liquid crystal composition; or
5) Compounds which control the colored display and orientation of the mixed liquid crystal composition.

For compounds which belong to the category
1) in this classification, compounds with a so-called PCH structure such as:

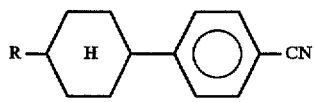

(Japanese examined patent publication (Tokko) Sho 56-38146),

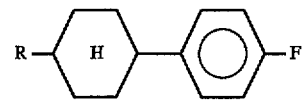

(Tokko Sho 64-373) and

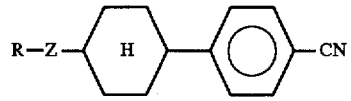

(Tokko Hei 1-38772) have been known.

Further, one of the basic components conventionally known which controls the electro-optical performance is a compound which has a so-called cyclohexyl ring -cyclohexyl ring-phenyl structure (CCP structure) with a mono- or di-fluoroalkyl chain(s) such as:

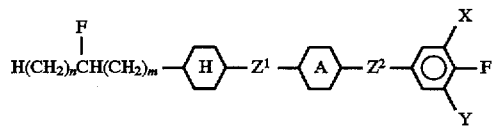

(Japanese unexamined patent publication Tokkai Hei 6-184019) and

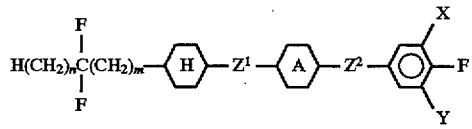

(Tokkai Hei 6-192142).

In recent years, along with the expansion of the applications of liquid crystal displays, the characteristics required of liquid crystal materials are becoming more and more advanced and demanding. In particular, superior characteristics such as improved low temperature performance, a wider temperature range for automobile onboard use and a lower driving voltage, compared with conventional liquid crystal substances, are desired.

BRIEF SUMMARY OF THE INVENTION

The object of the invention is to provide a newly developed liquid crystal substance with the PCH structure containing a silacyclohexane ring, targeting improvement in the characteristics of "1) compounds which contribute to a reduction in viscosity and a lowering of the melting point of the mixed liquid crystal composition".

The other object of the invention is to provide a newly developed liquid crystal substance with the aforementioned cyclohexyl ring-cyclohexyl ring-phenyl structure (CCP structure).

The present invention in one aspect provides a silacyclohexane compound represented by the following general formula (I):

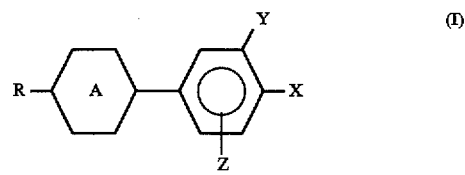

wherein R denotes a mono- or di-fluoroalkyl group with 1–10 carbons;

denotes a trans-1-silacyclohexylene or a trans-4-silacyclohexylene group whose silicon at position 1 or position 4 has a substitutional group of H, F, Cl or $CH_3$; X denotes a CN, F, Cl, $CF_3$, $CF_2Cl$, $CHFCl$, $OCF_3$, $OCHF_2$, $OCF_2Cl$, $OCHFCl$, $(O)_6CY_1=CX_1X_2$ ($X_1$ and $Y_1$ denote H, F or Cl, and $X_2$ denotes F or Cl), $(O)_sC_pH_qF_r$ (p denotes 2, 3 or 4, and q and r are integers which satisfy the equation $q+r=2p+1$, and s denotes 0 or 1), the aforementioned R, or an alkyl or alkoxy group with 1–5 carbons; Y denotes H or F; and Z denotes H or F.

This invention also provides a method of preparing the silacyclohexane compound represented by said general formula (I) characterized by the use of a reaction between an organo- metallic reagent R-M (M denotes MgP (P denotes a halogen), ZnP or Li) and a silacyclohexane compound:

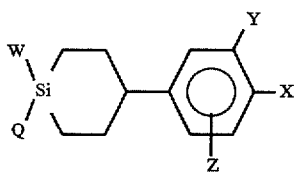

wherein W denotes M, F, Cl or a $CH_3$ group. Q denotes a halogen or an alkoxy group.

This invention also provides a method of preparing the silacyclohexane compound represented by said general formula (I) characterized by the use of a reaction between an organo- metallic reagent:

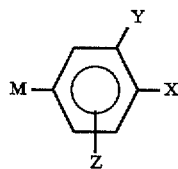

and a silacyclohexane compound:

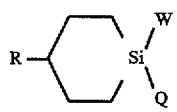

This invention also provides a method of preparing the silacyclohexane compound represented by said general formula (I) wherein X is CN, characterized by the use of a reaction between an organometallic reagent:

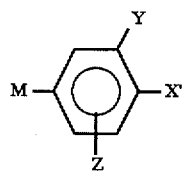

(wherein M denotes MgP' (P' denotes Br or I), Zn or Li, and X' denotes a halogen) and a silacyclohexane compound:

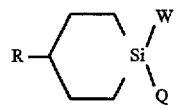

to obtain a phenylsilacyclohexane compound:

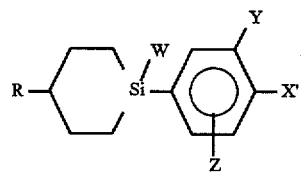

from which a Grignard's reagent is made, which is then reacted with a cyanogenation agent.

This invention in another aspect provides a silacyclohexane compound represented by the following general formula (II):

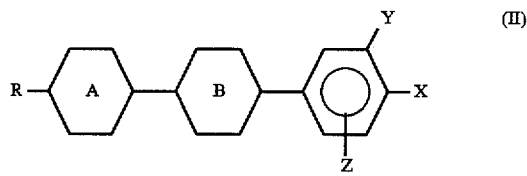

(II)

wherein R denotes hydrogen or a mono- or di-fluoroalkyl group with 1–10 carbons;

and

at least one of the two denotes a trans-1-silacyclohexylene or a trans-4-silacyclohexylene group whose silicon at position 1 or position 4 has a substitutional group of H, F, Cl or $CH_3$ and the other denotes a trans-1, 4-cyclohexylene group, a trans-1-silacyclohexylene group or a trans-4-silacyclohexylene group; X denotes a CN, F, Cl, $CF_3$, $CF_2Cl$, $CHFCl$, $OCF_3$, $OCHF_2$, $OCF_2Cl$, $OCHFCl$, $(O)_sCY_1=CX_1X_2$ ($X_1$ and $Y_1$ denote H, F or Cl, and $X_2$ denotes F or Cl), $(O)_sC_pH_qF_r$ (p denotes 2, 3 or 4, and q and r are integers which satisfy the equation $q+r=2p+1$, and s denotes 0 or 1), a mono- or di-fluoroalkyl group with 1–10 carbons, or an alkyl or alkoxy group with 1–5 carbons; Y denotes H or F; and Z denotes H or F.

This invention also provides a method of preparing the silacyclohexane compound represented by said general formula (II) characterized by the use of a reaction between an organometallic reagent R-M (M denotes MgP (P denotes a halogen), ZnP or Li) and a silacyclohexane compound:

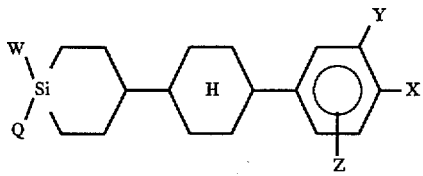

wherein W denotes H, F, Cl or a CH₃ group, and Q denotes a halogen or an alkoxy group with preferably 1–4 carbons.

This invention also provides a method of preparing the silacyclohexane compound represented by said general formula (II) characterized by the use of a reaction between an organometallic reagent:

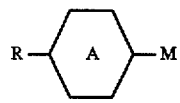

and a silacyclohexane compound:

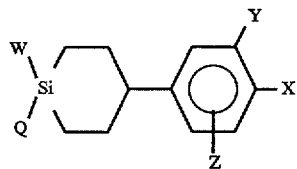

wherein:

denotes a trans-1-silacyclohexylene or a trans-4-silacyclohexylene group whose silicon at position 1 or position 4 has a substitutional group of H, F, Cl or CH₃, or a cyclohexylene group; W denotes H, F, Cl or a CH₃ group; and Q denotes a halogen or an alkoxy group with preferably 1–4 carbons.

This invention also provides a liquid crystal composition characterized by containing the silacyclohexane compound represented by said general formulas (I) or (II), and a liquid crystal display element characterized by containing this liquid crystal composition.

DETAILED DESCRIPTION

The present invention is further described in details below.

The compounds represented by said general formula (I), which have a ring structure with a trans-1 or 4-silacyclohexane ring, are specifically represented by ring structures:

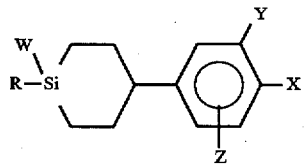

or

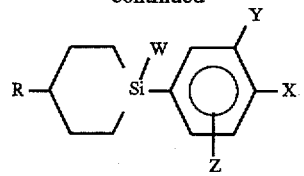

The new compounds represented by said general formula (II) which have a ring structure with at least one trans -1 or 4-silacyclohexane ring, are specifically represented by ring structures:

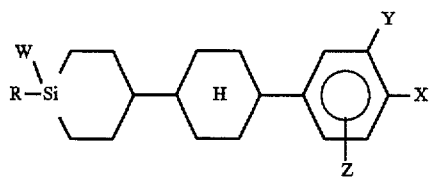

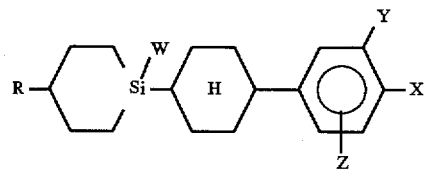

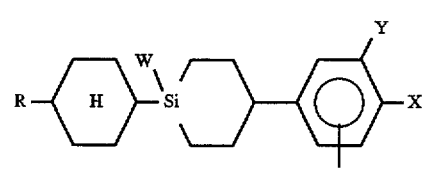

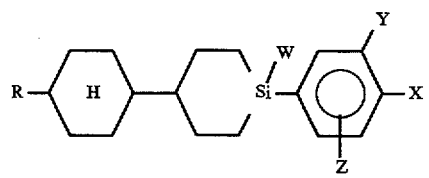

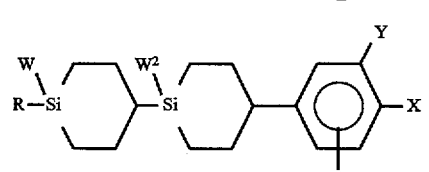

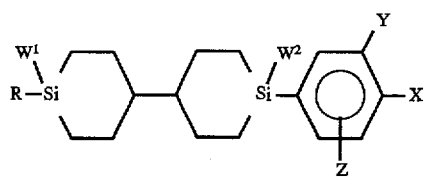

or

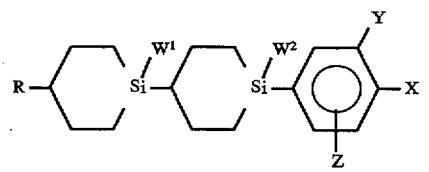

In these formulas, R denotes a mono- or di-fluoroalkyl group with 1–10 carbons, i.e. fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl or 10,10-dithiorodecyl group.

W, $W^1$ and $W^2$ independently denote H, F, Cl or $CH_3$.

X denotes a CN, F, Cl, $CF_3$, $CF_2Cl$, CHFCl, $OCF_3$, $OCHF_2$, $OCF_2Cl$, OCHFCl. $(O)_qCY_1=CX_1X_2$ ($X_1$ and $Y_1$ denote H, F or Cl, and $X_2$ denotes F or Cl), $(O)_sC_pH_qF_r$ (p denotes 2, 3 or 4, and q and r are integers which satisfy the equation $q+r=2p+1$, and s denotes 0 or 1), the aforementioned R or an alkyl or alkoxy group with 1–5 carbons.

Y denotes H or F. Z denotes H or F.

Specific examples of:

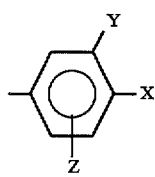

include the following groups:

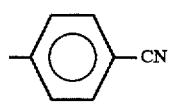

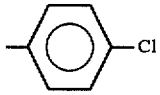

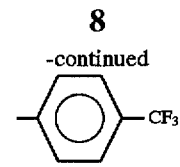

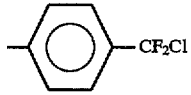

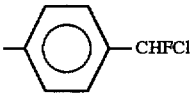

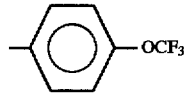

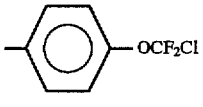

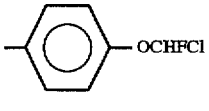

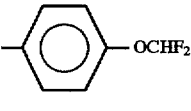

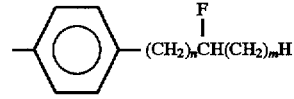

(each n and m denote an integer of 0–9 where n+m is 1–9.).

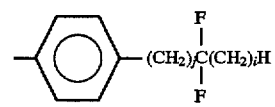

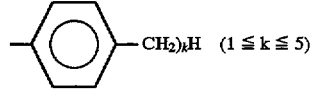

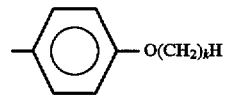

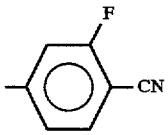

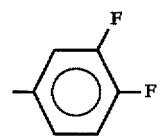

-continued

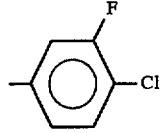
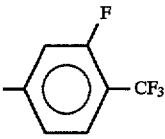
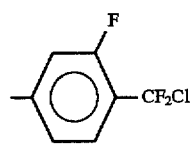
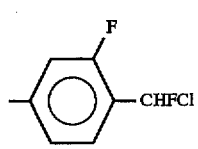
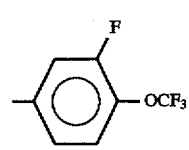
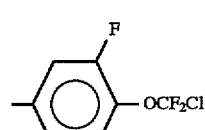
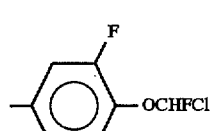
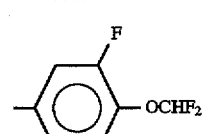
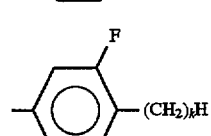
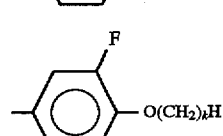
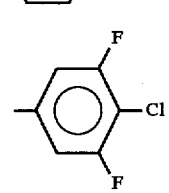

-continued

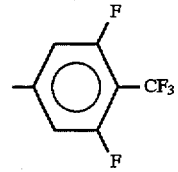
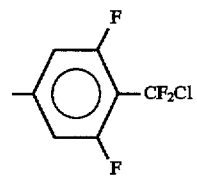
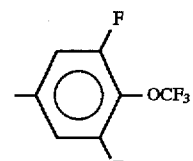
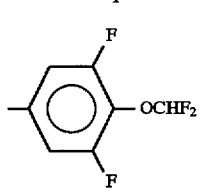
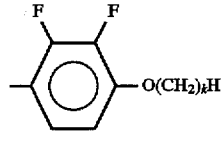
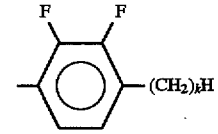

For R, 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-floorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl groups are desirable for practical use.

H, F and $CH_3$ groups are desirable for W in practical use. However, when the ring structure of the silacyclohexane ring is:

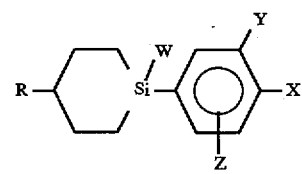

and X is a compound of CN, then W is limited to H or a $CH_3$ group.

For the group:
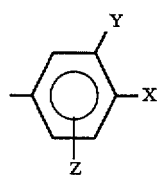
either group shown below is desirable:
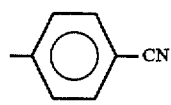
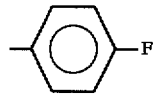
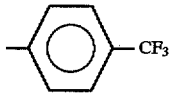
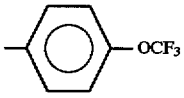
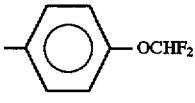
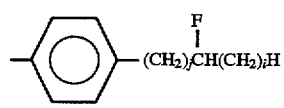
(each j and i denotes an integer of 0–9 where $1 \leq j+i \leq 9$.)
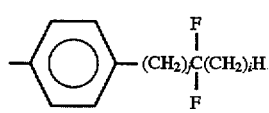
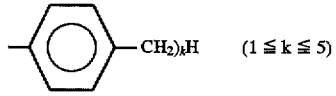   ($1 \leq k \leq 5$)
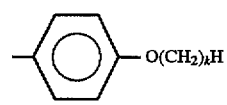
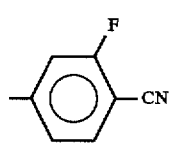
-continued
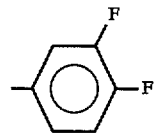
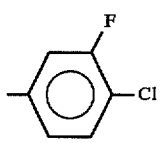
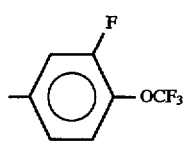
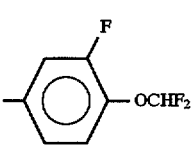
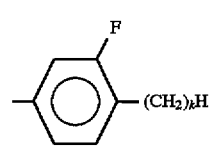
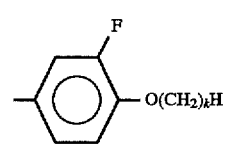
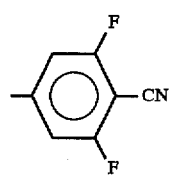
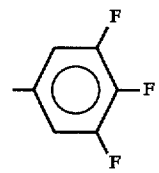
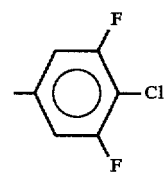
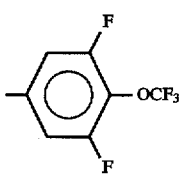

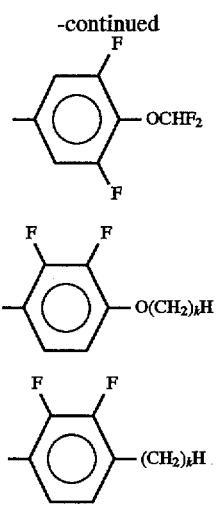

The manufacturing methods of the compounds represented by the formula (I) are described next. (1) A method of preparing the compound of this invention when the ring structure of the silacyclohexane ring is:

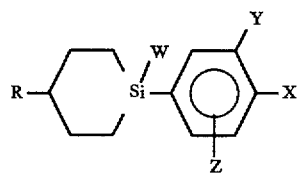

and X is CN.

In this preparation method, p-halobromobenzene or p-haloiodobenzene with substitutional groups Y and Z is brought into reaction with magnesium in a solvent such as THF (tetrahydrofuran) to obtain the corresponding Grignard's reagent, which is then brought into reaction with a silacyclohexane compound whose silicon has the substitutional groups W and Q. The product is again brought into reaction with magnesium metal in a solvent such as TMF (tetrahydrofuran) to prepare Grignard's reagent, which is then brought into reaction with a cyanogenation reagent such as cyanogen. The compound produced here is a mixture of trans isomers and cis isomers in Terms of the configuration of the silacyclohexane ring. A conventional purification means such as chromatography and recrystallization is employed to separate and purify the trans isomers to obtain the silacyclohexane compound of this invention represented by the general formula (I). The reaction formula is shown below.

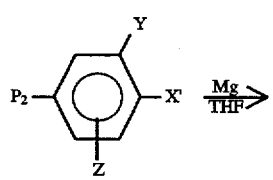

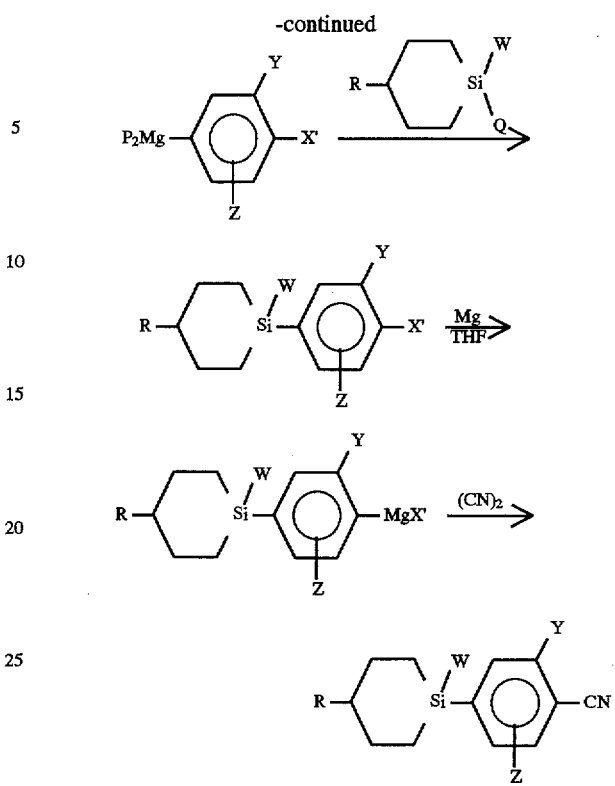

($P_2$ preferably denotes Br or I; X' denotes a halogen which is preferably Cl, Br or I; and Q denotes a halogen or an alkoxy group with preferably 1–4 carbons.) (2) A method of preparing the compound of this invention other than (1) as described above.

Although the reaction substrates are somewhat different depending on the ring structure, all of them are prepared using the coupling reactions of organometallic reagents shown below.

In this preparation method, R-halide or substituted aryl halide is used in a solvent such as THF (tetrahydrofuran) to obtain the corresponding organometallic reagent. The organometallic reagent thus produced is then brought into reaction with a silacyclohexane compound whose silicon has the substitutional groups W and Q. The compound produced here is a mixture of trans isomers and cis isomers in terms of the configuration of the silacyclohexane ring. A conventional purification means such as chromatography and recrystallization is employed to separate and purify the trans isomers to obtain the silacyclohexane compound of this invention represented by the general formula (I). The reaction formula is shown below,

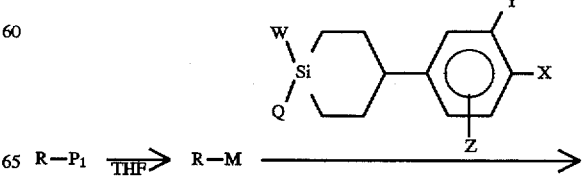

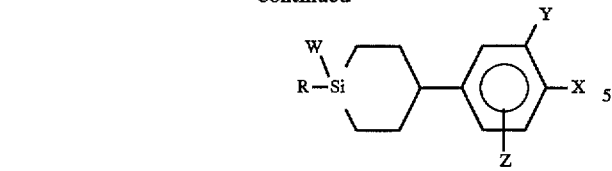

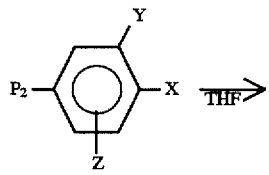

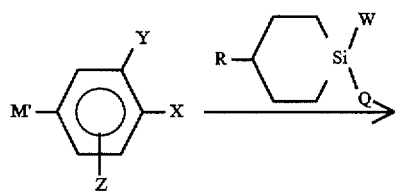

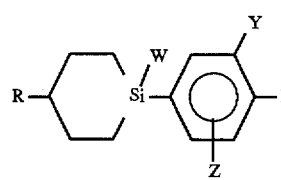

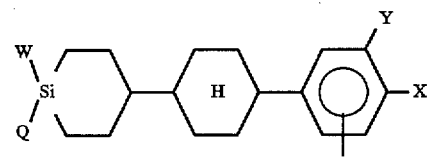

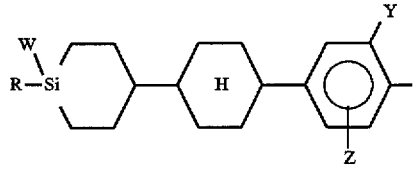

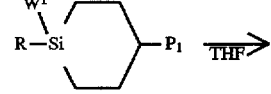

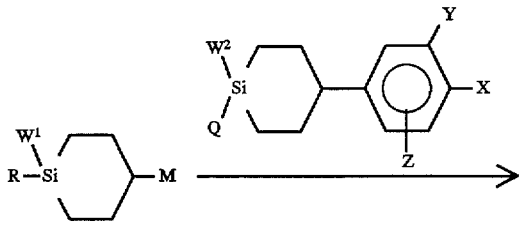

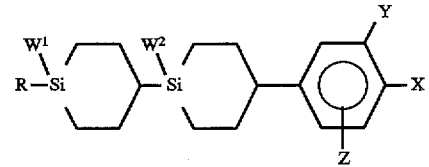

{M denotes MgP$_1$ (P$_1$ denotes a halogen which is preferably Cl, Br or I), ZnP$_1$ or Li; M' denotes Mg (P$_2$ preferably denotes Br or I (when X is Cl), or Cl, Br or I (when X is not Cl)), ZnP$_2$ or Li; Q denotes a halogen or alkoxy group with preferably 1–4 carbons; and W denotes a H, F, Cl or CH$_3$ group. X denotes a CN, F, Cl, CF$_3$, CF$_2$Cl, CHFCl, OCF$_3$, OCHF$_2$, OCF$_2$Cl, OCHFCl, (O)$_s$CY$_1$=CX$_1$X$_2$ (X$_1$ and Y$_1$ denote H, F or Cl, and X$_2$ denotes F or Cl), (O)$_2$C$_p$H$_q$F$_r$ (p denotes 2, 3 or 4, and q and r are integers which satisfy the equation q+r=2p+1, and s denotes 0 or 1), R or an alkyl or alkoxy group with 1–5 carbons. Y denotes H or F. Z denotes H or F. If W=F or Cl, then W=Q.}

The manufacturing methods of the compounds represented by the formula (II) are described next. Although the reaction substrates are somewhat different depending on the ring structure, all of them are prepared using the organometallic coupling reactions shown below.

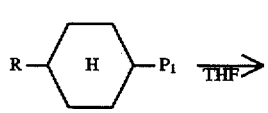

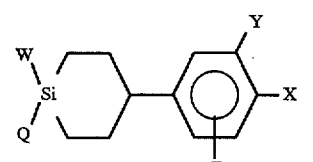

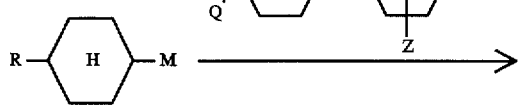

P$_1$ denotes a halogen which is preferably Cl, Br or I; Q denotes a halogen or an alkoxy group with preferably 1–4 carbons; M: MgP (P denotes a halogen), ZnP or Li, (If W=F or Cl, or W$^2$=F or Cl, then W=Q, W$^2$=Q, and W$^1$≠F or Cl)

In the preparation method described above, a cyclohexyl halide, R-halide or silacyclohexyl halide in a solvent such as THF (tetrahydrofuran) is used in a conventional manner to obtain the corresponding organometallic reagent. When doing this, an appropriate metal species is chosen according to the type of the substitutional group X. The metal halide thus produced is then brought into reaction with a silacyclohexane compound whose silicon has the substitutional groups W or W$^2$ and Q. The compound produced here is a mixture of trans isomers and cis isomers in terms of the conformation of the silacyclohexane ring. A conventional purification means such as chromatography and recrystallization is employed to separate and purify the trans isomers to obtain the silacyclohexane compound of this invention represented by the general formula (II).

The silacyclohexane compound of this invention can be mixed with known compounds to obtain a liquid crystal composition. The compound used for mixing to obtain the liquid crystals compound can be chosen from among the known compounds shown below:

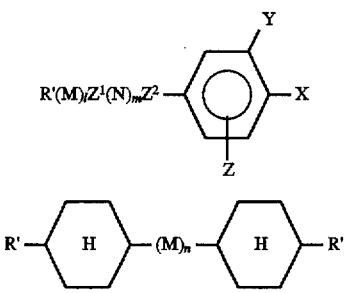

In the above formulas, (M) and (N) denote one of the following:
1) A trans-1,4-cyclohexylene group which has no substitution or which has one or more substitutional groups such as F, Cl, Br, CN or alkyl groups;
2) A ring comprising a cyclohexane ring in which O or S is substituted for one or nonadjacent two $CH_2$ groups;
3) A 1,4-cyclohexenylene group;
4) A 1,4-phenylene group which has no substitution or which has one or two substitutional groups chosen from among F, Cl, CN, and CN groups; or
5) A ring comprising a 1,4-phenylene group in which an N atom is substituted for one or two CH groups.

$Z^1$ and $Z^2$ denote $-CH_2CH_2-$, $-CH=CH-$, $-C\equiv C-$, $-CO_2-$, $-OCO-$, $-CH_2O-$, $-OCH_2-$ or a single bond.

l, m=0, 1 or 2 (where l+m=1, 2 or 3, and n=0, 1 or 2)

R' denotes hydrogen, a linear chain alkyl group with 1–10 carbons, a branched-chain alkyl group with 3–8 carbons, an alkoxyalkyl group with 2–7 carbons, a mono- or di- fluoroalkyl group with 1–10 carbons or an alkenyl group with 2–8 carbons.

X, Y and Z are the same as defined for the general formulas (I) or (II).

In the above description, if f or n=2, then (M) can contain heterogeneous rings, and if m=2, then (N) can contain heterogeneous rings.

The ratio of one or more types of the silacyclohexane compound of this invention contained in the liquid crystal composition is 1–50 mol %, more preferably 5–30 mol %. The liquid crystal composition can also contain a polygoneric dye(s) to generate the colored guest-host system and additives to change the dielectric anisotropy, viscosity and the orientation of the nematic phase.

The liquid crystal composition thus formed can be used to manufacture various liquid crystal display elements in conventional methods. That is, the liquid crystal composition containing the silacyclohexane compound of this invention is sealed between transparent plates which have electrodes of desired shapes and thus used as liquid crystal display elements. This element can have various undercoatings, overcoatings for the orientation control, a polarizer plate(s), a filter(s) and a reflector layer(s), as necessary. It can be made into a laminated cell or combined with other display elements. Semiconductor substrates and light sources can also be used to make various types of displays.

For the driving method of the liquid crystal display element, prior-art methods in the industry of liquid crystal display elements, such as the dynamic scattering (DSM) method, the twisted nematic (TN) method, the guest-host (GH) method, the super twisted nematic (STN) method and the polymer dispersion liquid crystal (PDLC) method can be adopted.

The silacyclohexane compounds of this invention have a strong tendency to show an enantiotropic phase transition when their substitutional group X is CN. When the substitutional group X is not CN, most of them show a monotropic phase transition or a crystal -isotropic liquid type transition, and do not show the electro-optical characteristics of liquid crystals when used separately. However, they contribute to a reduction in the viscosity and a lowering of the melting point when used with other liquid crystal compounds in a liquid crystal composition.

By using the liquid crystal compounds of this invention which have Si as a ring composing element as components of a liquid crystal composition, reduction of the viscosity, improvement of the response time and improvement of compatibility in low temperatures can be achieved.

Also, liquid crystal compounds whose X in the general formula (I) is neither R nor OR have, in addition to the advantages mentioned above, an effect of lowering the threshold voltage because of a greater dielectric anisotropy.

The liquid crystal compound whose substitutional group X in the general formula (I) is an alkyl group, an alkoxyalkyl group, R or OR has near-zero negative dielectric anisotropy, and therefore it should preferably be used for the liquid crystal phase for display based on the dynamic scattering (DS) or deformation of aligned phase (DAP mode). The compounds in which X is other than an alkyl group, an alkoxyalkyl group, R or OR should preferably be used for manufacturing the liquid crystal phase with a large positive dielectric anisotropy which is used in display elements based on the twisted nematic cell or the cholesteric-nematic phase transition.

The liquid crystal compounds of the present invention which have Si as a ring composing element have the following advantages over liquid crystal compounds which have a conventional CCP structure comprising similar hydrocarbon rings:

(1) Because they have the nematic liquid crystal phase extended to lower temperatures, the following low temperature characteristics improve.

(2) The viscosity in a low temperature range drops, resulting in the improved response time in the low temperature range.

(3) Compatibility in a low temperature range improves.

Also, liquid crystal compounds whose X in the general formula (II) is neither R nor OR have, in addition to the advantages mentioned above, an effect of lowering the threshold voltage.

The threshold voltage can be lowered by increasing the dielectric anisotropy ($\Delta\epsilon$) of the liquid crystal compound. The compounds of the present invention have an advantage of having a lower threshold voltage compared with the prior art compounds with the same $\Delta\epsilon$.

The liquid crystal compounds of this invention, depending on the selection of their substitutional groups, can be widely used as the base material which comprises the major component of the liquid crystal phase, in a manner similar to how the conventional liquid crystal compounds with a CCP structure of similar hydrocarbon rings are used. The liquid crystal compound whose substitutional group X in the general formula:

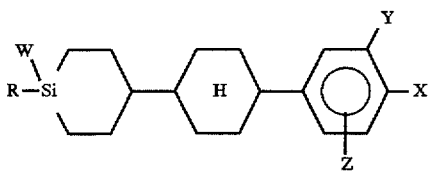

is R or OR has near –zero dielectric anisotropy, and therefore it should preferably be used for the liquid crystal phase for display based on the dynamic scattering (DS) or deformation of aligned phase (DAP mode). The compounds in which X is other than R or OR should preferably be used for manufacturing the liquid crystal phase with a large positive dielectric anisotropy which is used in display elements based on The Twisted nematic cell or the cholesteric-nematic phase transition.

EXAMPLES

The details of this invention are described below by referring to specific examples.

Example 1

Preparation of 4-(trans-4-n-(4-fluoropentyl)-4-silacyclohexyl) benzonitrile 3.4 g (20 mmol) of 1-bromo-4-fluoropentane was dripped into a mixture of 0.5 g of magnesium (21 mmol) and 50 ml of THF to obtain Grignard's reagent. This solution was then added to a mixture of 2.8 g of zinc chloride and 20 ml of THF to obtain the organic zinc reagent. This solution was then dripped into a 50 ml THF solution of 4.7 g (20 mmol) of 4 -(4-chloro-4-silacyclohexyl) benzonitrile to obtain 4-(4-(4-fluoropentyl)-4-silacyclohexyl) benzonitrile.

This product was a mixture of trans isomers and cis isomers with regard to the silacyclohexane ring. They were separated by means of chromatography to obtain 5.3 g of the trans isomers (yield 92%).

Example 2

Preparation of 4-(trans-4-(7-fluoroheptyl)-4-silacyclohexyl) -1, 2-difluorobenzene ene 3.0 g (20 mmol) of 1-bromo-7-fluoroheptane was dripped into a mixture of 0.5 g of magnesium (21 mmol) and 50 ml of THF to obtain Grignard's reagent. This reagent was then dripped into a 50 ml THF solution of 4.9 g (20 mmol) of 4-(4-chloro-4-silacyclohexyl) -1.2-difluorobenzene to obtain 4-(4-(7-fluoroheptyl)-4-silacyclohexyl)-1,2-difluorobenzene.

This product was a mixture of trans isomers and cis isomers with regard to the silacyclohexane ring. They were separated by means of chromatography to obtain 6.1 g of the trans isomers (yield 93%).

Example 3

4-(trans-4-(4-fluoroheptyl)-4-silacyclohexyl)-1-fluorobenzene

The above compound was obtained in the same manner as Example 2, using 4-(4-chloro-4-silacyclohexyl)-1-fluorobenzene instead of 4-(4-chloro-4-silacyclohexyl)-1,2-difluorobenzene, with 1-bromo-7-fluoroheptane. IR (liquid film) ν max: 920, 2873, 2100, 1510, 1227, 985, 887 and 820 $cm^{-1}$.

C-N transition temperature: 27° C.

Example 4

4-(trans-4-(4-fluoroheptyl)-4-silacyclohexyl)-1-chlorobenzene

The above compound was obtained in the same manner as Example 2, using 4-(4-chloro-4-silacyclohexyl)-1-fluorobenzene instead of 4-(4-chloro-4-silacyclohexyl)-1, 2-difluorobenzene, with 1-bromo-7-fluoroheptane.

Example 5

4-(trans-4-methoxypentyl-1-silacyclohexyl)1-difluoromethoxybenzene

The above compound was obtained in the same manner as Example 2, using 4-(4-chloro-4-silacyclohexyl)-1-fluoromerhoxybenzene instead of 4-(4-chloro-4-silacyclohexyl)-1,2-difluorobenzene, with 1-bromo-7-fluoroheptane.

The compounds of this invention obtained in the examples described above were added to existing liquid crystal compositions to prepare liquid crystal compositions of this invention. For the obtained liquid crystal compositions, the threshold voltage and the viscosity at 20° C. were measured.

Example 6

Preparation of 4-(trans-4-(trans-4-(4-fluorobutyl) cyclohexyl-4-silacyclohexyl)-1,2-difluorobenzene 4.7 g (20 mmol) of 4-(4-fluorobutyl) cyclohexyl bromide was dripped into a mixture of 0.5 g of magnesium (21 mmol) and 50 ml of THF to obtain Grignard's reagent. This solution was then dripped into 50 ml THF solution of 4.9 g (20 mmol) of 4-(4-chloro-silacyclohexyl)-1,2-difluorobenzene to obtain 4-(4-(trans-4-n-propylcyclohexyl)-4-silacyclohexyl)-1,2-difluorobenzene. This product was a mixture of trans isomers and cis isomers with regard to the silacyclohexane ring. They were separated by means of chromatography to obtain 6.7 g of the trans isomers (yield 91%).

Example 7

4-(trans-4-(trans-4-(4,4-difluorobutyl) cyclohexyl)-4-silacyclohexyl)-1-fluorobenzene The above compound was obtained in the same manner as Example 6, using 4-(4, 4-difluorobutyl)cyclohexylbromide and 4-(4-chloro-4-silacyclohexyl)-1-fluorobenzene instead of 4-(4-fluorobutyl)cyclohexylbromide and 4-(4-chloro-4-silacyclohexyl)-1, 2-difluorobenzene, respectively.

Example 8

4-(trans-4-(trans-4-(4,4-difluorobutyl)cyclohexyl)-4-silacyclohexyl)-1-chlorobenzene The above compound was obtained in the same manner as Example 6, using 4-(4,4-difluorobutyl)cyclohexylbromide and 4-(4-chloro-4-silacyclohexyl)-1-chlorobenzene instead of 4-(4-fluorobutyl)cyclohexybromide and 4-(4-chloro-4-silacyclohexyl)-1,2-difluorobenzene, respectively.

Example 9

4-(trans-4-(trans-4-(4-fluoropentyl) cyclohexyl)-4-silacyclohexyl)-1-trifluoromethoxybenzene The above compound was obtained in the same manner as Example 6, using 4-(4-fluoropentyl)cyclohexylbromide and 4-(4-chloro-4-silacyclohexyl)-1-trifluoromethoxybenzene instead of 4-(4-fluorobutyl)cyclohexylbromide and 4-(4-chloro-4-silacyclohexyl)-1,2-difluorobenzene, respectively.

Example 10

4-(trans-4-(trans-4-(4-fluorobutyl) cyclohexyl)-4-silacyclobexyl)-1,2,6-trifluorobenzene The above compound was obtained in the same manner as Example 6, using 4-(4-chloro-4-silacyclohexyl)-1,2,6-trifluorobenzene instead of 4-(4-chloro-4-silacyclohexyl)-1,2-difluorobenzene, with 4-(4-fluorobutyl) cyclohexylbromide.

Example 11

4-(trans-4-methyl-4-(trans-4-(3-fluoropropyl) cyclohexyl)-4-silacyclohexyl)-1-methoxybenzene The above compound was obtained in the same manner as Example 6, using 4-(3-fluoropropyl)cyclohexylbromide and 4-(4-chloro-4-methyl-4-silacyclohexyl)anisole instead of 4-(4-fluorobutyl)cyclohexylbromide and 4-(4-chloro-4-silacyclohexyl)-1,2-difluorobenzene, respectively.

Example 12

4-(trans-4-methyl-4-(trans-4-(3-fluoropropyl) cyclohexyl)-4-silacyclohexyl)-1-chloro-2,6-difluorobenzene The above compound was obtained in the same manner as Example 6, using 4-(3-fluoropropyl)cyclohexylbromide and 4-(4-chloro-4-methyl-4-silacyclohexyl)-1-chloro-2,6-difluorobenzene instead of 4-(4-fluorobutyl) cyclohexylbromide and 4-(4-chloro-4-silacyclohexyl)-1,2-difluorobenzene, respectively.

Example 13

4-(trans-4-(trans-4-(4-fluorobutyl) cyclohexyl)-4-silacyclohexyl) benzonitrile 4.7 g (20 mmol) of 4-(4-fluorobutyl) cyclohexyl bromide was dripped into a mixture of 0.5 g of magnesium (21 mmol) and 50 ml of THF to obtain Grignard's reagent. This solution was then added to a mixture of 3.0 g (22 mmol) of zinc chloride and 10 ml of TMF to obtain the organic zinc reagent. This reagent was then dripped into a 50 ml THF solution of 4.7 g (20 mmol) of 4-(4-chloro-4-silacyclohexyl) benzonitrile to obtain 4-(4-(trans-4-n-propylcyclohexyl)-4-silacyclohexyl) benzonitrile. This product was a mixture of trans isomers and cis isomers with regard to the silacyclohexane ring. They were separated by means of chromatography to obtain 5.9 g of the trans isomers (yield 83%).

Example 14

4-(trans-4-(trans-4-(4-fluoropentyl)-4-silacyclohexyl) cyclohexyl)-1-difluoromethoxy-2,6-difluorobenzene 3.4 g (20 mmol) of 4-fluoropentyl bromide was dripped into a mixture of 0.5 g of magnesium (21 mmol) and 50 ml of TMF to obtain Grignard's reagent. This solution was then dripped into a 50 ml THF solution of 7.9 g (20 mmol) of 4-(4-(4-chloro-4-silacyclohexyl)-trans-4-cyclohexyl)-1-difluoromethoxy-2,6-difluorobenzene to obtain 4-(trans-4-(trans-4-n-pentyl-4-silacyclohexyl)-4-cyclohexyl)1-difluoromethoxy-2,6-difluorobenzene. This product was a mixture of trans isomers and cis isomers with regard to the silacyclohexane ring. They were separated by means of chromatography to obtain 7.4 g of the trans isomers (yield 90%).

Example 15

4-(trans-4-(trans-4-(3-fluoropropyl)-4-silacyclohexyl) cyclohexyl)-1-fluorobenzene The above compound was obtained in the same manner as Example 14. using 3-fluoropropylbromide and 4-(4-(4-chloro-4-silacyclohexyl)-trans-4-cyclohexyl)-1-fluorobenzene instead of 4-fluoropentylbromide and 4-(4-(4-chloro-4-silacyclohexyl)-trans-4-cyclohexyl)-1-difluoromethoxy-2,6-difluorobenzene, respectively.

Example 16

4-(trans-4-(trans-4-(4-fluorobutyl)-4-silacyclohexyl) cyclohexyl)-1,2-difluorobenzene The above compound was obtained in the same manner as Example 14, using 4-fluorobutylbromide and 4-(4-(4-chloro-4-silacyclohexyl)-trans-4-cyclohexyl)-1-fluorobenzene instead of 4-fluoropentylbromide and 4-(4-(4-chloro-4-silacyclohexyl)-trans-4-cyclohexyl)-1-difluoromethoxy-2,6-difluorobenzene, respectively.

IR (liquid film) p max: 2924, 2852, 2100, 1518, 1277, 1207, 987, 887 and 822 cm$^{-1}$ C-N transition temperature: 11° C., N-I transition temperature: 67° C.

Example 17

4-(trans-4-(trans-4-(4-fluorobutyl)-4-silacyclohexyl)-4-cyclohexyl)-1-trifluoromethoxybenzene The above compound was obtained in the same manner as Example 14, using 4-fluorobutylbromide and 4-(4-(4-chloro-4-silacyclohexyl)-trans-4-cyclohexyl)-1-trifluoromethoxybenzene instead of 4-fluoropentylbromide and 4-(4-(4-chloro-4-silacyclohexyl)-trans-4-cyclohexyl)-1-difluoromethoxy-2,6-difluorobenzene, respectively.

IR (KBr disc) v max: 2924, 2852, 2110, 1510, 1265, 1221, 1192, 1161, 985, 887 and 827 cm$^{-1}$ C-N transition temperature: 43° C., N-I transition temperature: 97° C., S-N transition temperature: 32° C.

Example 18

4-(trans-4-(trans-4-(3-fluoropropyl)-4-silacyclohexyl) cyclohexyl)-1-chloro-2-fluorobenzene The above compound was obtained in the same manner as Example 14, using 3-fluoropropylbromide and 4-(4-(4-chloro-4-silacyclohexyl)-trans-4-cyclohexyl)-1-chloro-2-fluorobenzene instead of 4-fluoropentylbromide and 4-(4-(4-chloro-4-silacyclohexyl)-trans-4-cyclohexyl)-1-difluoromethoxy-2,6-difluorobenzene, respectively.

Example 19

4-(trans-4-(trans-4-(4-fluorobutyl )-4-silacyclohexyl) cyclohexyl)-2,3-difluoro-1-ethoxybenzene The above compound was obtained in the same manner as Example 14, using 4-fluorobutylbromide and 4-(4-(4-chloro-4-silacyclohexyl)-trans-4-cyclohexyl)-2,3-difluoro-1-ethoxybenzene instead of 4-fluoropentylbromide and 4-(4-(4-chloro-4-silacyclohexyl)-trans-4-cyclohexyl)-1-difluoromethoxy-2,6-difluorobenzene, respectively.

Example 20

4-(trans-4-(trans-4-(3-fluoropropyl)-4-silacyclohexyl) cyclohexyl)-1-(4-fluorobutyl) benzene The above compound was obtained in the same manner as Example 14, using 1-bromopropane and 4-(4- (4-chloro-4-silacyclohexyl)-trans-4-cyclohexyl)-1-(4-fluorobutyl) benzene instead of 4-fluoropentylbromide and 4-(4-(4-chloro-4-silacyclohexyl)-trans-4-cyclohexyl)-1-difluoromethoxy-2,6-difluorobenzene, respectively.

Example 21

4-(trans-4-(trans-4-(4-fluorobutyl)-4-silacyclohexyl) cyclohexyl)-1-difluoromethoxy-2,6-difluorobenzene The above compound was obtained in the same manner as Example 14, using 4-fluorobutylbromide and 4-(4-(4-chloro-4-silacyclohexyl)-trans-4-cyclohexyl)-1-difluoromethoxy-2,6-difluorobenzene instead of 4-fluoropentylbromide and 4-(4-(4-chloro-4-silacyclohexyl)-trans-4-cyclohexyl)-1-difluoromethoxy-2,6-difluorobenzene, respectively.

IR (KBr disc) v max: 2927, 2856, 2106, 1516, 1148, 1097, 1065, 1034, 889 and 812 cm$^{-1}$ C-N transition temperature: 52° C., N-I transition temperature: 80° C.

Example 22

4-(trans-4-(trans-4-(4,4-difluorobutyl)-4-silacyclohexyl)-4-silacyclohexyl)-1-trifluoromethylbenzene 5.4 g (9.0 mmol) of 4-(4,4-difluorobutyl) silacyclohexyl bromide was dripped into a mixture of 0.5 g of magnesium (21 mmol) and 50 ml of THF to obtain Grignard's reagent. This solution was then dripped into a 50 ml THF solution of 5.6 g (20 mmol) of 4-(4-chloro-4-silacyclohexyl)-1-trifluoromethylbenzene to obtain 4-(4-(4-n-propylsilacyclohexyl)-4-silacyclohexyl)-1-trifluoromethylbenzene. This product was a mixture of trans isomers and cis isomers with regard to the silacyclohexane ring. They were separated by means of chromatography to obtain 4 g of the trans isomers (yield 85%).

Example 23

4-(trans-4-(trans-4-(3-fluoropropyl)-4-silacyclohexyl)-4-silacyclohexyl)-1-n-propylbenzene The above compound was obtained in the same manner as Example 23, using 4-(3-fluoropropyl)-4-silacyclohexylbromide and 4-(4-chloro-4-silacyclohexyl)-1-n-propylbenzene instead of 4-(4,4-difluorobutyl)-4-silacyclohexylbromide and 4-(4-chloro-4-silacyclohexyl)-1-trifluoromethoxybenzene, respectively.

Example 24

4-(trans-4-(trans-4-(4-fluorobutyl)-4-methyl-4-silacyclohexyl)-1-trifluoromethoxy-2-fluorobenzene The above compound was obtained in the same manner as Example 23, using 4-(4-fluorobutyl)-4-silacyclohexylbromide and 4-(4-chloro-4-methyl-4-silacyclohexyl)-1-trifluoromethoxy-2-fluorobenzene instead of 4-(4,4-difluorobutyl)-4-silacyclohexylbromide and 4-(4-chloro-4-silacyclohexyl)-1-trifluoromethoxybenzene, respectively.

The compounds of this invention obtained in the examples described above were added to existing liquid crystal compositions to prepare liquid crystal compositions of this invention. For the obtained liquid crystal compositions, the threshold voltage and the transition temperature were measured.

Example of the liquid crystal composition

A mixture A which comprises 40 mole % of 4-(4-(trans-4-ethylcyclohexyl)-trans-4-cyclohexyl)-1,2-difluorobenzene, 35 mol % of 4-(4-(trans-4-n-propylcyclohexyl)-trans-4-cyclohexyl)-1,2-difluorobenzene and 25 mol % of 4-(4-(trans-4-n-pentylcyclohexyl)-trans-4-cyclohexyl)-1,2-difluorobenzene exhibits characteristics listed below.

C-N transition temperature: 7° C.
N-I transition temperature: 106° C.
Threshold voltage: 2.50 V A mixture which comprises 80% of this mixture A and 20 mol % of 4-(trans-4-(trans-4-(4-fluorobutyl)-4-silacyclohexyl) cyclohexyl)-1-trifluoromethoxybenzene from Example 12 exhibited characteristics listed below.

C-N transition temperature: 0° C.
N-I transition temperature: 104° C.
Threshold voltage: 2.34 V

What is claimed is:

1. A silacyclohexane compound represented by the following general formula (I):

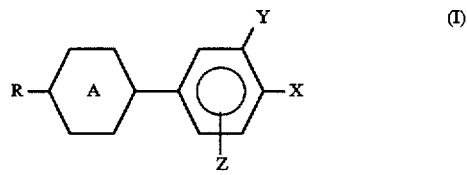

wherein R denotes a mono- or di-fluoroalkyl group with 1–10 carbons;

denotes a trans-1-silacyclohexylene or a trans-4-silacyclohexylene group whose silicon at position 1 or position 4 has a substitutional group of H, F, Cl or CH$_3$;

X denotes a CN, F, Cl, CF$_9$CF$_2$Cl, CHFCl, OCF$_9$, OCHF$_2$, OCF$_2$Cl, OCHFCl, (O)$_s$CY$_1$=CX$_1$X$_2$ (X$_1$ and Y$_1$ denote H, F or Cl, and X$_2$ denotes F or Cl), (O)$_s$C$_p$H$_q$F$_4$ (p denotes 2, 3 or 4, and q and r are integers which satisfy the equation q+r=2p+1, and s denotes 0 or 1), the aforementioned R, or an alkyl or alkoxy group with 1–5 carbons;

Y denotes H or F; and

Z denotes H or F.

2. A method of preparing the silacyclohexane compound as described in claim 1 characterized by the use of a reaction between an organometallic reagent R-M (M denotes MgP (P denotes a halogen), ZnP or Li) and a silacyclohexane compound:

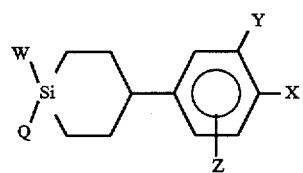

wherein W denotes H, F, Cl or a CH$_3$ group, and Q denotes a halogen or an alkoxy group having 1–4 carbon atoms.

3. A method of preparing the silacyclohexane compound as described in claim 1 characterized by the use of a reaction between an organometallic reagent:

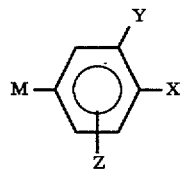

wherein M denotes MgP denotes a halogen, ZnP or Li and a silacyclohexane compound:

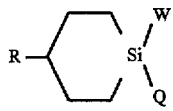

wherein Q denotes a halogen or an alkoxy group having 1–4 carbon atoms; and W denotes H, F, Cl or a CH₃ group.

4. A method of preparing the silacyclohexane compound as described in claim 1 wherein X is CN, characterized by the use of a reaction between an organometallic reagent:

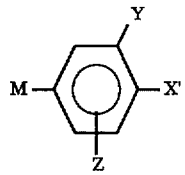

(M denotes MgP' (P' denotes Br or I), ZnP' or Li, and X'denotes a halogen) and a silacyclohexane compound:

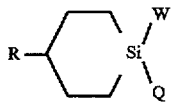

wherein Q denotes a halogen or an alkoxy group having 1–4 carbon atoms, and W denotes H, F, Cl or CH₃ group to obtain a phenylsilacyclohexane compound:

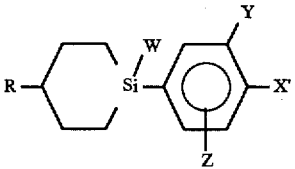

which is then reacted with MR to form a Grignard's reagent which is then reacted with a cyanogenation agent.

5. A silacyclohexane compound represented by the following general formula (II):

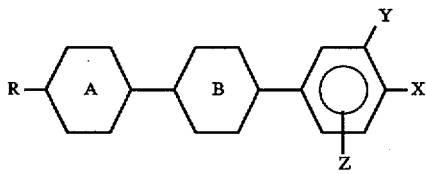

(I)

wherein R denotes a mono- or di-fluoroalkyl group with 1–10 carbons;

at least one of

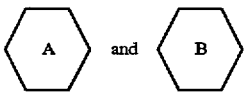

denotes a trans-1-silacyclohexylene or a trans-4-silacyclohexylene group whose silicon at position 1 or position 4 has a substitutional group of H, F, Cl or CH₃ and the other denotes a trans-1,4-cyclohexylene group, a trans-1-sila-1,4-cyclohexylen group or a trans-4-sila-1,4-cyclohexylene group;

X denotes a CN, F, Cl, CF₃, CF₂Cl, CHFCl, OCF₃, OCHF₂, OCF₂Cl, OCHFCl, the aforementioned R, or an alkyl or alkoxy group with 1–5 carbons;

Y denotes H or F; and

Z denotes H or F.

6. A method of preparing the silacyclohexane compound as described in claim 5 characterized by the use of a reaction between an organometallic reagent R-M (M denotes MgP (P denotes a halogen), ZnP or Li) and a silacyclohexane compound:

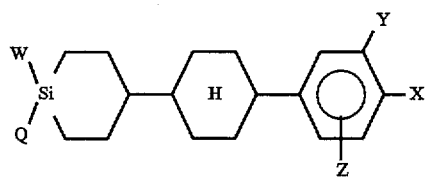

Wherein W denotes H, F, Cl or a CH₃ group, and Q denotes a halogen or an alkoxy group having 1–4 carbon atoms.

7. A method of preparing the silacyclohexane compound as described in claim 5 characterized by the use of a reaction between an organometallic reagent:

wherein M denotes MgP (P denotes a halogen, ZnP or Li) and a silacyclohexane compound:

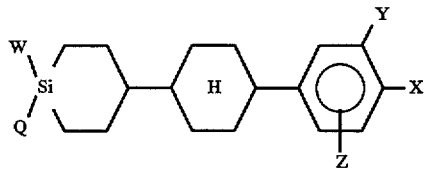

wherein

denotes a trans-1-silacyclohexylene or a trans-4-silacyclohexylene group whose silicon at position 1 or position 4 has a substitutional group of H, F, Cl or CH₃, or a cyclohexylene group;

W denotes H, F, Cl or a CH₃ group; and

Q denotes a halogen or an alkoxy group having 1–4 carbon atoms.

8. A liquid crystal composition characterized by containing the silacyclohexane compound as described in claim 1.

9. A liquid crystal display element characterized by containing the liquid crystal composition as described in claim 8.

10. A liquid crystal composition characterized by containing the silacyclohexane compound as described in claim 5.

11. A liquid crystal display element characterized by containing the liquid crystal composition as described in claim 10.

* * * * *